(12) United States Patent
Carpenter

(10) Patent No.: US 11,291,412 B2
(45) Date of Patent: Apr. 5, 2022

(54) INTEGRATED CIRCUIT MEDICAL DEVICES AND METHOD

(71) Applicant: Vactronix Scientific, LLC, Fremont, CA (US)

(72) Inventor: Scott P. Carpenter, Fremont, CA (US)

(73) Assignee: Vactronix Scientific, LLC., Freemont (CA)

( * ) Notice: Subject to any disclaimer, the term of this patent is extended or adjusted under 35 U.S.C. 154(b) by 101 days.

(21) Appl. No.: 16/781,932

(22) Filed: Feb. 4, 2020

(65) Prior Publication Data
US 2020/0245946 A1 Aug. 6, 2020

Related U.S. Application Data

(60) Provisional application No. 62/801,018, filed on Feb. 4, 2019.

(51) Int. Cl.
| | |
|---|---|
| *A61B 5/00* | (2006.01) |
| *A61F 2/91* | (2013.01) |
| *H01L 21/02* | (2006.01) |
| *H01L 23/29* | (2006.01) |
| *H01L 23/31* | (2006.01) |
| *A61B 5/30* | (2021.01) |

(52) U.S. Cl.
CPC .............. *A61B 5/6862* (2013.01); *A61B 5/30* (2021.01); *A61B 5/4064* (2013.01); *A61B 5/6868* (2013.01); *A61F 2/91* (2013.01); *H01L 21/02266* (2013.01); *H01L 23/293* (2013.01); *H01L 23/3178* (2013.01); *A61F 2210/0014* (2013.01); *A61F 2210/0076* (2013.01); *A61F 2240/001* (2013.01); *A61F 2250/0096* (2013.01)

(58) Field of Classification Search
CPC .......................................................... A61F 2/91
See application file for complete search history.

(56) References Cited

U.S. PATENT DOCUMENTS

| | | | | |
|---|---|---|---|---|
| 6,264,687 | B1 * | 7/2001 | Tomonto ................. | A61F 2/915 623/1.16 |
| 2007/0056151 | A1 * | 3/2007 | Koch ...................... | A61F 2/915 29/282 |
| 2014/0180397 | A1 * | 6/2014 | Gerberding ............. | A61F 2/852 623/1.16 |
| 2014/0277382 | A1 * | 9/2014 | Dolan ...................... | A61F 2/91 623/1.16 |
| 2019/0091048 | A1 * | 3/2019 | Pung ....................... | A61F 2/848 |

FOREIGN PATENT DOCUMENTS

| | | | | |
|---|---|---|---|---|
| EP | 2953550 | | 5/2020 | ............. A61B 17/00 |
| WO | WO2013163503 | | 10/2013 | ............... A61N 1/05 |

OTHER PUBLICATIONS

International Search Report and Written Opinion issued in corresponding foreign application, PCT/US2020/016658, pp. 1-13 (dated Jun. 8, 2020).

\* cited by examiner

*Primary Examiner* — Benjamin P Sandvik
(74) *Attorney, Agent, or Firm* — Rosenbaum IP, P.C.; David G. Rosenbaum

(57) ABSTRACT

A universal implantable integrated circuit medical device platform having integral and monolithic circuit traces. The platform allows for implanting into a mammalian body single and multi-functional interface devices for sensing, monitoring stimulating and/or modulating physiological conditions within the body. Microelectronic circuitry may be integrated onto the platform or may be joined as modular components to the platform.

20 Claims, 12 Drawing Sheets

INTEGRATED CIRCUIT MEDICAL DEVICES AND METHOD

CROSS-REFERENCE TO RELATED APPLICATION

The present application claims priority to U.S. provisional application Ser. No. 62/801,018 filed Feb. 4, 2019, herein incorporated by reference in its entirety.

BACKGROUND OF THE INVENTION

The present invention pertains generally to interface devices for sensing and/or modulating physiological activity in a mammalian body. More particularly, the present invention pertains to a medical device capable of delivery to anatomical passageways and other spaces or regions within a body, including, without limitation central or peripheral venous or arterial systems, epidural, subdural, subarachnoid, arachnoid, cerebral sinus spaces, subcutaneous, transcutaneous, intramuscular, body cavities, and/or central or peripheral nervous systems. Even more particularly, the present invention relates to an apparatus for physiologically interfacing with body fluid and/or tissue in any of the aforementioned anatomical passageways or other spaces or regions within the body. Still more particularly, the present invention pertains to a universal multi-functional platform configured to single-function or multi-functional components integrated monolithically or added to the platform.

Disorders of the central and peripheral nervous system may arise as a result of disease or trauma and many manifests themselves in abnormal or disrupted electrical activity in neural or nerve circuits. Dysregulated or uncontrolled recurrent nerve activity is implicated in such conditions such as, for example, epilepsy, cardiac rhythm disturbances, postural orthostatic tachycardia syndrome, neurocardiogenic syncope, or vasovagal syncope. Traumatic injury, such as stroke, spinal cord injury, peripheral nerve injury often operates by disrupting the electrical pathways and disconnecting a neural component; examples of traumatic neural injury include diminished or lost motor or sensory function. Finally, neurodegenerative diseases, such as Parkinson's disease, myasthenia gravis, multiple sclerosis, for example, are characterized by cessation of neuronal function in discrete regions, leading to diminished function in the neural circuits associated with the discrete regions.

When the electrical lesion is focal, effective diagnosis and treatment of such conditions depends on precise localization of the lesion and, when possible, restoration of normal electrophysiologic function to the affected region.

A variety of well-established techniques exist for localizing electrical lesions in the brain, each of which has specific limitations. (1) Imaging techniques such as magnetic resonance imaging (MM) and computed tomography (CT) constitute entirely noninvasive methods of examining brain tissue, and many functional lesions (including strokes, anatomic abnormalities capable of causing seizures, and foci of neuronal degeneration) can be detected and precisely localized using such imaging modalities. Not all functional lesions can be detected using these imaging modalities, however, as these techniques do not image electrical activity. Furthermore, these imaging techniques lack temporal resolution, and provide no mechanism for therapeutic electrophysiologic intervention. (2) Electromagnetic recording techniques such as electroencephalography (EEG) and magnetoencephalography (MEG) are entirely noninvasive techniques that provide excellent temporal resolution of electrical activity in the brain. For this reason, EEG is currently the gold standard modality for detection of seizure activity. The spatial resolution of such techniques is limited, however, both due to physical distance of electrodes from the brain, and by the dielectric properties of scalp and skull. The spatial resolution of EEG is better for superficial regions, and worse for neural activity deep within the brain. (3) Electrocorticography (ECoG), or intracranial EEG, is a form of electroencephalography that provides improved spatial resolution by placing recording electrodes directly on the cortical surface of the brain (in conventional EEG, by contrast, electrodes are positioned on the scalp). This modality is frequently used during neurosurgical procedures to map normal brain function and locate abnormal electrical activity, but it requires craniotomy, temporary surgical removal of a significant portion of the skull, in order to expose the brain surfaces of interest, and exposes patients to the attendant risks of brain surgery. Furthermore, while electrical activity near the cortical surface of the brain can be mapped with reasonable spatial resolution, electrical activity deep within the brain remains difficult to localize using ECoG. (4) "Depth electrodes" record electrical activity with high spatial and temporal precision, but such electrodes record only from small volumes of tissue (small populations of neurons), and their placement requires disruption of normal brain tissue along the trajectory of the electrode, resulting in irreversible damage or destruction of some neurons. As such electrodes are placed surgically, in a hypothesis-driven manner, the number of such electrodes that can be safely placed simultaneously is limited. (5) Deep brain stimulation (DBS) electrodes, the stimulating analog of recording depth electrodes, electrically stimulate brain regions with millimetric precision. They are implanted using minimally invasive surgical techniques, and can be effective in conditions such as Parkinson's disease, in which neuronal dysfunction is confined to a small, discrete, and unambiguous region of the brain.

SUMMARY OF THE INVENTION

The present invention is useful in a wide variety of applications and indications. For example, the universal platform of the present invention may be used as an active and/or passive sensor at an implantation site within the body. The present invention may be configured as one or more of a biosensor, flow sensor, thermal sensor, pressure sensor, electrode, electrical sensor, or the like. The universal platform includes a framework support member that is configured into a tubular shape, a planar shape or into complex geometric shapes conforming to the body region into which it is implanted. The framework support member has a plurality of openings passing through a thickness of the framework support member 3 which are configured to geometrically deform to allow for multi-axial compliance and flexibility of the framework support member. The plurality of openings bound a plurality of structural members in the framework support member. A plurality of slots is present in at least some of the structural members. The slots define circuit traces in the structural members. A dielectric material is filled into the slots to electrically isolate the circuit traces from the remainder of the structural member in which the slot opening is present. A coating of the dielectric material covers the framework support member and leaves exposed regions of circuit traces for a passive or active sensor on one end of the circuit trace and for an electrical connection to the circuit traces at an opposing end of the circuit traces. The framework support member is preferably fabricated of an electrically conductive shape memory or superelastic material.

It is an objective of the present invention to provide a platform for single or multi-functional interface with soft and hard tissue within a body.

In one aspect, the present application discloses an implantable medical device with a flexible substrate and an array of active and/or passive sensors mounted on the flexible substrate for interface with the desired regions within the body.

In some embodiments, scaffold may be a tubular stent or a generally planar structure. The sensor array may be integrated onto or into the scaffold. The sensors in the sensor array may be monolithic with the scaffold or be discrete elements that are coupled to the scaffold. The sensor array may be periodic with sensor groupings positionally mapped on the scaffold. In some embodiments, the conformal scaffolding can be continuous. In some embodiments, the implantable medical device further includes an on-board power source, microprocessor, transceiver and antenna.

In another aspect of the invention, the present application discloses a method of making an integrated circuit device including in some embodiments the steps of: depositing a layer of an electrically conductive material, which may be a plastically deformable, shape memory or superelastic material, onto a substrate; forming a plurality of slots passing through the deposited layer of electrically conductive material thereby defining a plurality of circuit traces bounded by at least one slot of the plurality of slots; coating a dielectric layer onto the deposited layer of electrically conductive material having the plurality of slots and the plurality of circuit traces formed therein and filling the plurality of slots; and selectively removing regions of the dielectric layer to expose at least one section of each trace of the plurality of circuit traces. It will be understood by one skilled in the art that by depositing the electrically conductive material onto the substrate, the bond between the electrically conductive material and the substrate retains the electrically conductive material on the substrate when the plurality of slots are formed. In this manner, the non-slotted regions of the electrically conductive material do not release from the substrate when the slots are formed.

In another aspect, the present application discloses a method for electrically, physically, or chemically interacting with a body tissue using sensor array located.

In yet another aspect of the invention, the method can include selecting a portion of neural tissue for electrophysiological interface, accessing positional information of the electrode array within the brain, selecting at least one electrode or electrode grouping in the electrode array for electrophysiological interface based upon the positional information, activating the at least one electrode or electrode grouping in the electrode array to electrophysiologically interface with the desired region of the brain.

In some embodiments, the method can include stimulating the body tissue, or recording electrical, physical or chemical activities of the body tissue, or simultaneously stimulating and recording activities of the body tissue. In some embodiments, the method can include forming an electrical field beam distributed in a three-dimensional space using the selected electrodes. In some embodiments, the method can include localizing electrical activity in the brain using the selected electrode distributed in a three-dimensional space.

In some embodiments, the method can include localizing electrical activities from epileptogenic foci within a hippocampus for the management of epilepsy. In some embodiments, the method can include stimulating the brain in response to epileptogenic activity within the hippocampus for the management of epilepsy. In some embodiments, the method can include interacting with motor pathways by an electrical field generated by the electrode array at a distance to assist in restoring mobility and limb control. In some embodiments, the method can include stimulating visual pathways to generate visual perception. In some embodiments, the method can include stimulating sensory cortex or sensory thalamus to deliver sensory stimulation to the brain for a neurosensory prosthesis or for the treatment of thalamic pain. In some embodiments, the method can include stimulating hypothalamic nuclei for the management of neuroendocrine disorders, circadian rhythm disorders, physiologic response to fever or hypothermia, or obesity. In some embodiments, the method can include registering the electrode array to obtain its orientation and position within the ventricular compartment of a brain via neuroimaging. In some embodiments, the method can include placing the electrode array into the ventricular compartment of a brain via a minimally invasive insertion technique, such as a cannula or catheter.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE PREFERRED EMBODIMENTS

Figure 1A:
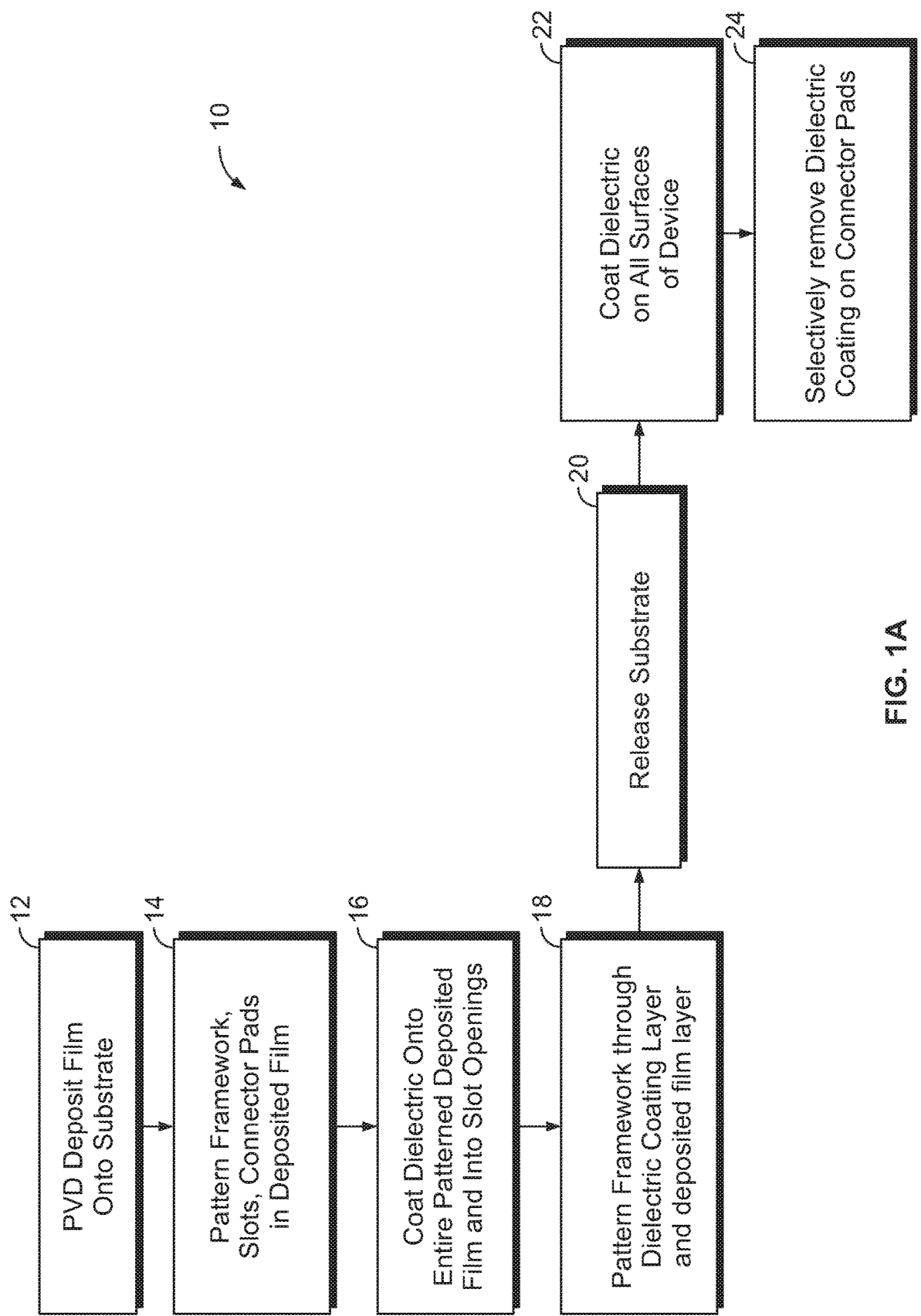
FIGS. 1A-1B are flow diagrams depicting methods of making the integrated circuit medical devices according to the present invention.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

"Substantially" is intended to mean a quantity, property, or value that is present to a great or significant extent and less than totally.

"Shape memory alloy" is intended to mean a binary, ternary, quaternary metal alloy that recover apparent permanent strains when raised above a martensitic transformation temperature ($M_s$). Shape memory alloys have two stable phases, i.e., a high-temperature or austenite phase and a low-temperature or martensite phase.

"Superelastic" is intended to mean a property of a material characterized by having a reversible elastic response in response to an applied stress. Superelastic materials exhibit a phase transformation between the austenitic and martensitic phases as the applied stress is loaded or unloaded.

"Active sensor" is intended to mean a sensing device requiring a power source to send and receive signals.

"Passive sensor" is a sensor device that detects and responds to some type of input from the physical environment in which the sensor is placed. A passive sensor is a device that detects and responds to some type of input from the physical environment.

"Sensor" in the singular or plural is intended to include active sensors or passive sensors and include, without limitation, biosensors, flow sensors, thermal sensors, pressure sensors, electrodes, microfluidic sensors and/or electrical sensors.

"Radiopaque" is intended to mean any material that obstructs passage of radiation and increases contrast to X-rays or similar radiation.

As depicted in the accompanying Figures, the integrated circuit medical device of the present invention is based upon a universal platform engineered to accommodate single or multi-functional additions to the universal platform. The universal platform includes a framework support member 32 having a plurality of openings configured to define structural members 34 between adjacent pairs of the plurality of openings. Each of the plurality of opening are geometrically deformable in the plane of the framework support member and impart multi-axial compliance to the framework support member. Each of the structural members 34 have a width, a depth and a length. The depth of each structural member is substantially equal to the depth of the framework support member 32. The width and length of each structural member is defined by the plurality of openings bounding each structural member. The framework support member 32, itself, may have a generally tubular shape, a generally planar shape or may be configured into more complex geometric shapes to conform to the space or region within the body in which the device will be implanted.

Figure 1B:
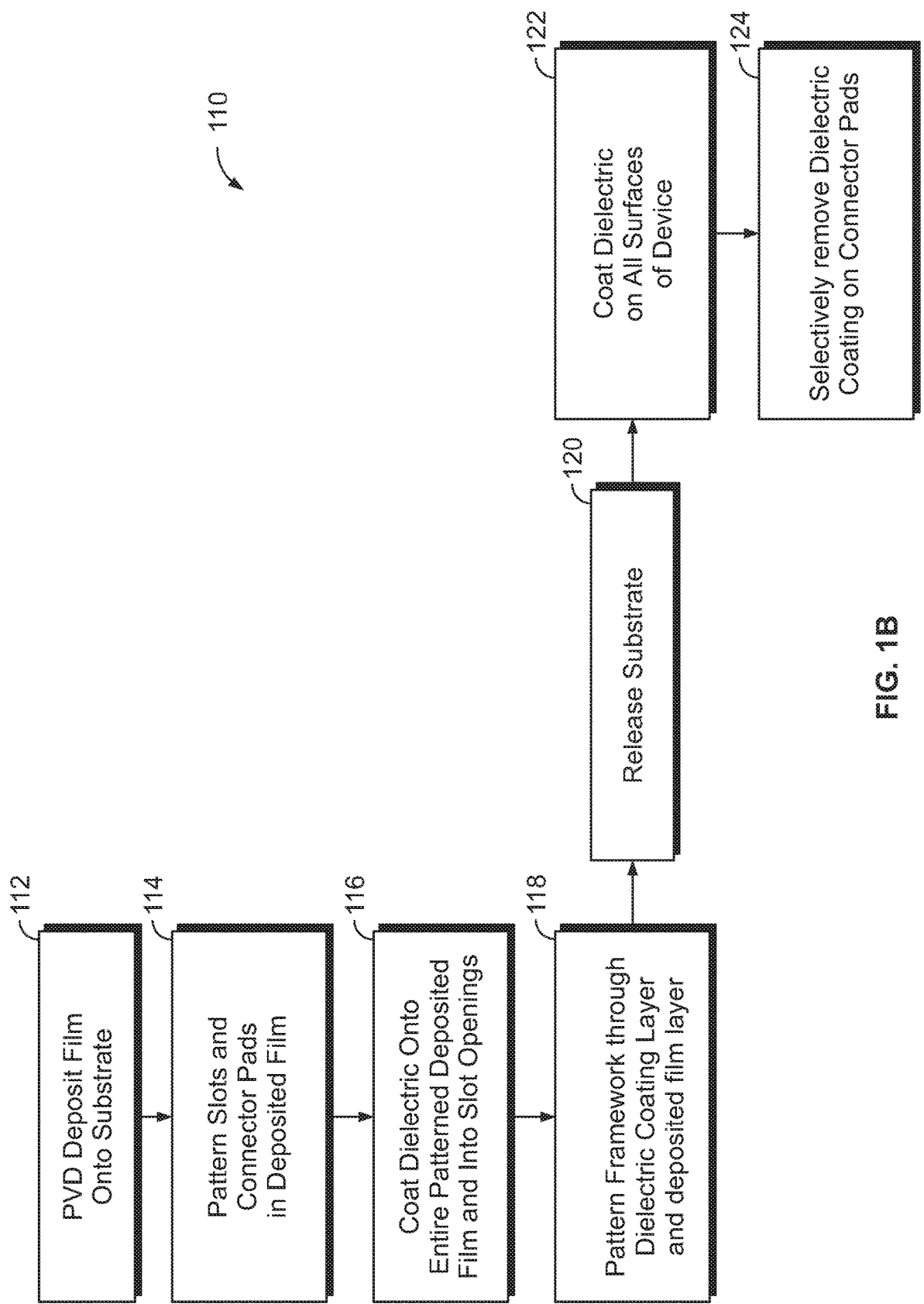

FIG. 1A and FIG. 1B are a process flow charts depicting the process steps for the method 10 of making the integrated circuit medical devices according to the present invention. As shown in FIG. 1A, in a first step, a film of device forming material is deposited by physical vapor deposition onto a substrate 12. Once the film is deposited, the framework, slots, connector pads are patterned into the deposited film 14. Patterning may be by any suitable method, including photolithography, chemical etching, electrical discharge machining, laser cutting, or the like. It has been found advantageous to pattern the film by employing laser machining using a femto-second laser. The laser machining for the framework, slots, traces, end pads and connector pads cuts through the entire thickness of the deposited film to the underlying substrate to define the respective structural members and circuit traces.

Once the deposited device forming material is patterned, the entire patterned deposited film is coated with a dielectric material which covers all outer surfaces of the patterned deposited film and fills in all slots with the dielectric material 16. The dielectric material may be solvated and either spray coated or dip coated onto the patterned deposited film and into the slots. Alternatively, the dielectric material may be deposited onto the patterned deposited film and into the slots by other low-temperature vacuum deposition processes.

Once fully coated with the dielectric material, the framework may be patterned again 18, and the underlying substrate is released 20 causing any islands in the pattern to fall away from the patterned framework. Then the entire patterned framework is coated on all surfaces 22, including coating over the first dielectric coating and any exposed surfaces of the patterned deposited film that had been in contact with the substrate. Once fully coated with the dielectric material, sections of the dielectric coating covering the end pads and connector pads are selectively removed 24 to expose the end pads and connector pads.

Alternatively, as shown in FIG. 1B, in a first step, a film of device forming material is deposited by physical vapor deposition onto a substrate 112. Once the film is deposited, slots, traces, and connector pads are patterned into the deposited film through to the substrate 114. Patterning may be by any suitable method, including photolithography, chemical etching, electrical discharge machining, laser cutting, or the like. It has been found advantageous to pattern the film by employing laser machining using a femto-second laser. The laser machining for the framework, slots, end pads and connector pads cuts through the entire thickness of the deposited film to the underlying substrate to define the respective structural members and circuit traces.

Once the slots, traces, and connector pads are patterned into the deposited film, the entire patterned deposited film is coated with a dielectric material which covers all outer surfaces of the patterned deposited film and fills in all slots with the dielectric material 116. The dielectric material may be solvated and either spray coated or dip coated onto the patterned deposited film and into the slots. Alternatively, the dielectric material may be deposited onto the patterned deposited film and into the slots by other low-temperature vacuum deposition processes.

Once fully coated with the dielectric material, the framework is patterned into the deposited film through the dielectric material layer to the substrate 118. Patterning may be by any suitable method, including photolithography, chemical etching, electrical discharge machining, laser cutting, or the like. It has been found advantageous to pattern the film by employing laser machining using a femto-second laser. The laser machining for the framework, slots, traces, end pads and connector pads cuts through the entire thickness of the deposited film to the underlying substrate to define the respective structural members and circuit traces.

With respect to FIG. 1A and FIG. 1B, it will be understood by one skilled in the art that by depositing the electrically conductive material onto the substrate, the bond between the electrically conductive material and the substrate retains the electrically conductive material on the substrate when the plurality of slots are formed. In this manner, the non-slotted regions of the electrically conductive material do not release from the substrate when the slots are formed.

After the framework patterning is completed, the underlying substrate is released 120 which causes any islands in the pattern to fall away from the patterned framework. Then the entire patterned framework is coated on all surfaces 122, including coating over the first dielectric coating and any exposed surfaces of the patterned deposited film that had been in contact with the substrate. Once fully coated with the dielectric material, sections of the dielectric coating covering the end pads and connector pads are selectively removed 124 to expose the end pads and connector pads.

In some embodiments of the method described in FIG. 1A and FIG. 1B, successive layers of traces and dielectric material may be deposited to a build multilayer circuit framework.

Furthermore, in order to maintain registration alignment between successive process steps, including patterning the traces or framework support member, it may be advantageous to apply an alignment marker for longitudinal and latitudinal alignment to the deposited electrically conductive material layer or subsequent layers. A single marker for the device, or a marker for each pattern may be employed to cut the various slots and framework patterns consistently.

Figure 2:
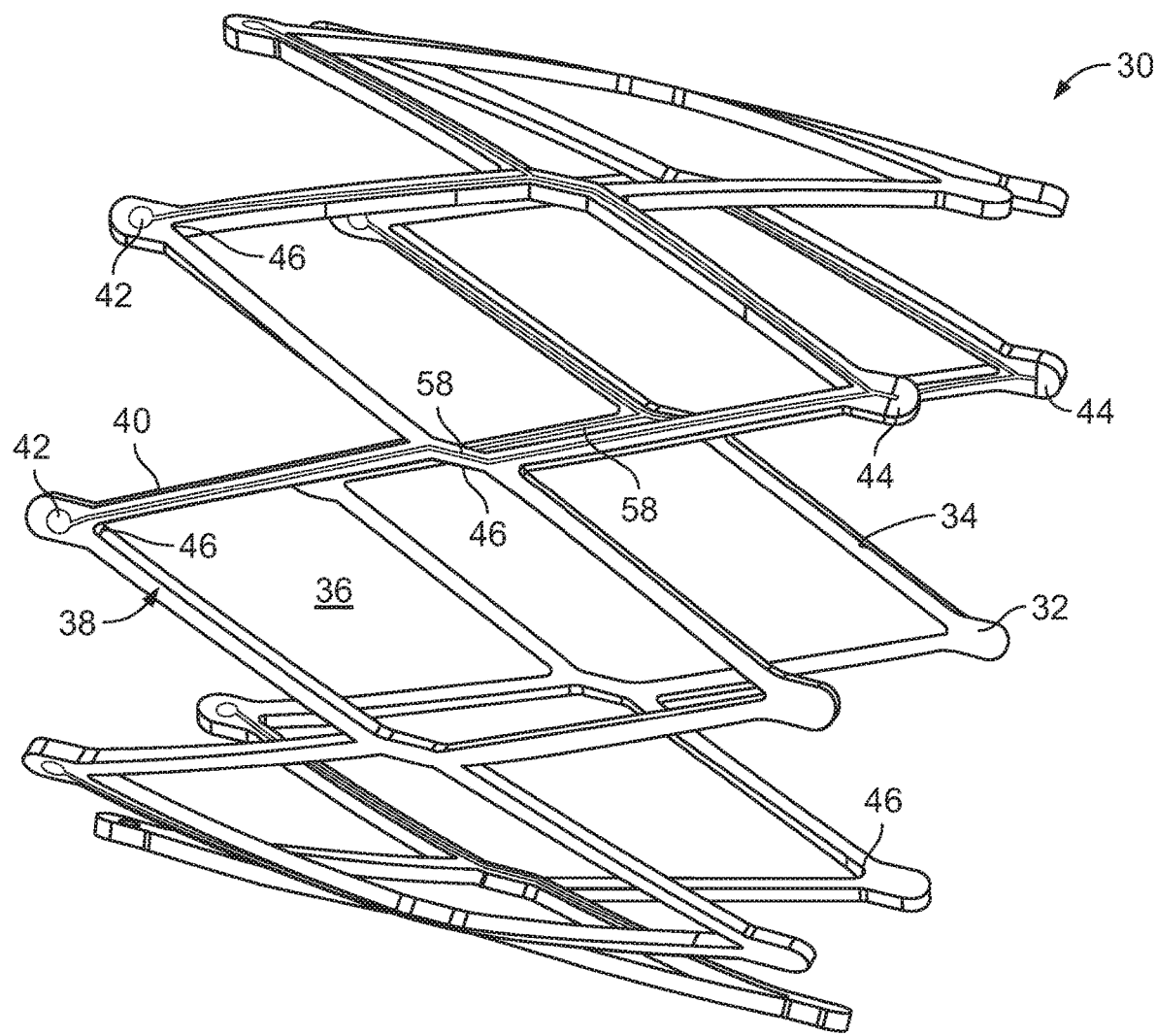
FIG. 2 is a perspective view of the integrated circuit medical device framework platform with structural members and integrally formed circuit traces in accordance with the present invention.

FIG. 2 depicts an exemplary integrated circuit medical device 30 in accordance with the present invention. While FIG. 2 depicts a tubular stent-like device, the present invention is not intended to be limited in geometry to a tubular stent-like device, and other geometric configurations such as, for example, planar, undulating, coiled, C-shaped, ribbon, or other complex geometries configured to adapt to anatomical structures, such as hard tissue surfaces or soft tissue surfaces, are intended to be within the scope of the present invention.

Integrated circuit medical device 30 is the end-product result of the method described above with reference to FIG. 1A and FIG. 1B. The integrated circuit medical device 30 consists generally of a framework support member 32 having a plurality of structural members 34 which may be articulated at a plurality of hinge regions 46 to allow for deformation of the structural members 34 and flexibility and compliance of the framework support member 32. The plurality of structural members 34 are separated by a plurality of interstitial opening 36 that may enlarge or diminish in open surface area as the framework support member 32 is deformed and recovers. A plurality of slots 58 pass through a thickness of and open to opposing wall surfaces of at least some structural members 34 of the plurality of structural members 34. The slots 58 may extend along a substantial longitudinal aspect of one or more structural members 34 and may pass across one or more of a plurality of hinge regions 46 in the framework support member 32. Circuit traces 40 are defined by an elongate portion of the structural support member bounded by bordering slots 58.

At least one dielectric material coating 38, such as polyimide, more particularly poly (4,4'-oxydiphenylene-pyromellitimide), commercially available under the tradename KAPTON (DuPont, Wilmington, Del., U.S.), covers all surfaces of the integrated circuit medical device 30, except that the connector pads 42, 44 are exposed through the dielectric material coating 38. The exposed connector pads 42 may, themselves, serve as electrodes or may be substrate points for a more complex electronic circuit to support an active or passive sensor, as will be more fully discussed below. It should be understood by one of skill in the art that the at least one dielectric material coating may comprise any biocompatible dielectric material that is capable of being patterned or cut with a femto-second laser. These materials may additionally include but are not limited to Parylene, ABS, Fluoropolymers such as: Polytetrafluoroethylene (PTFE), PTFE-S, Perfluoroalkoxy (PFA), Fluorinated Ethylene Propylene (FEP), PTFE PFA, PTFE FEP, Ethylene Tetrafluoroethylene (ETFE), and poly vinylydene fluoride (PVDF).

Connector pads, either electrodes 42 or electrical connector pads 44 are positioned at opposing ends of the circuit traces 40. Electrodes 42 or electrical connector pads 44 may also be positioned at intermediate positions along the longitudinal aspect of a circuit trace 40. Electrodes 42 and electrical connector pads 44 are electrically coupled to one another by the circuit trace 40 with which they are associated.

In accordance with preferred aspects of the present invention, the framework support member 32 has a thickness of between about $50\mu$ to about $175\mu$. The depth of each structural member 34 is also between about $50\mu$ to about $175\mu$, the width of each structural member is between about $25\mu$ to about $100\mu$ and the length of each structural member 34 may be between about $100\mu$ to about $5000\mu$.

At least some of the structural members 34 further include circuit traces 40 formed in the structural members 34 and are bounded by slots 58 passing through the entire thickness of the structural members. The slots 58, therefore, have a depth equal to the thickness of the structural members. In this manner, the circuit traces 40 are islands of the structural member 34 surrounded by the slots 58 and isolated from the structural members of the framework support member 32. The slots 58 are filled with a dielectric material 38 that both electrically isolates the circuit traces 40, electrodes 42 and electrical connector pads 44 from the structural members 34 of the framework support member 32 and structurally supports the circuit traces 40, electrodes 42 and electrical connector pads 44 as the framework support member 32 is deformed and/or flexed. In one embodiment, each circuit trace 40 may terminate on one end with an electrode 42 and at an opposing end with an electrical connection pad 44. The electrode 42 of the circuit trace is also bounded by a slot 58 and electrically isolated from the structural member 34 by the dielectric material 38. Similarly, each electrical connection pad 44 is electrically coupled only to the circuit trace 40 that it is associated with and is electrically isolated from other regions of the framework support member 32. The electrode 42 and the electrical connection pads 44 are each exposed through a coating of the dielectric material 38 which also covers the remainder of the outer surfaces of the framework support member 32. The connection pads 44 serve as electrical connection points to couple electrical leads to each of the circuit traces 40.

In accordance with preferred aspects of the present invention, the circuit traces 40 have a width between about $3\mu$ to about $80\mu$ depending upon the width of the structural member. The width of the circuit traces 40 is considered to be in inverse proportion to the thickness of the structural members 34 in which the circuit trace 40 is formed. Thus, for example, if the structural members 34 have a depth greater than $100\mu$, the circuit traces may have a width less than about $50\mu$. Moreover, depending upon the electrical signal demand of the integrated circuit, the circuit trace 40 and the structural members 34 may be relatively thicker or thinner. For example, where the integrated circuit is configured as an active sensor, the integrated circuit will require a power signal in addition to a bi-direction electrical signal. Thus, the circuit traces 40 to support such an active sensor will be relatively thicker in depth and/or wider in width than where the integrated circuit is configured as a passive sensor.

Furthermore, relatively narrower circuit traces 40 will enhance structural integrity of the framework support member 32 since the structural elements 34 will have more mass and, therefore, be relatively stiffer than where wider circuit traces 40 are employed. Additionally, where there is a mismatch between the Young's modulus of the support framework and structural members and the dielectric layer, deformation of the integrated circuit medical device will induce shear strain between the dielectric material 38 and the material of the framework support member 32 and structural members 34. Relatively thinner in depth and narrower in width circuit traces 40 will also serve to reduce the shear strain in the dielectric material 38 during such deformation events, such as will occur during loading the device into a delivery system, delivering the device in vivo, deploying the device in vivo, or resulting from deformation when the device resides within the body.

For example, the Young's modulus of Nitinol depends on the phase and thermomechanical processing of the Nitinol. It generally ranges from about 4 to about 14 GPa, with austenite Nitinol typically ranging between about 10 to about 14 GPa. For polyimide, more particularly poly (4,4'-oxydiphenylene-pyromellitimide), commercially available under the tradename KAPTON (DuPont, Wilmington, Del., U.S.), the Young's modulus ranges from about 2.0 to about 4 GPa at processing and body temperatures. Both Nitinol and the polyimide have non-linear stress-strain curves that ought to be considered when defining the particular construct and design of the inventive integrated circuit medical devices.

The connector pads 42, 44 may have multiple purposes. Where the material of the framework support 32 is electrically conductive, the connector pads 42 themselves may be configured as electrodes to sense and/or deliver electrical energy when juxtaposed to tissue within the body. The connector pads 44 may also serve as substrates or electrical connection pads onto which either integrally formed or coupled active or passive circuits may be associated. Non-limiting examples of active or passive circuits which may be employed with the present invention include: biosensors, pressure sensors, flow sensors, electrical sensors, thermal sensors, and/or electrodes.

The circuit traces 40 may be a single circuit trace 40 with a single electrode 42 and a single electrical connection pad 44 or may be branched such that a single circuit trace has plural electrodes 42 electrically coupled to a single connection pad 44 or plural electrical connection pads 44 using circuit traces 44 as electrical conduits between electrical devices and data acquisition devices. Further, a single circuit trace 40 may have intermediate electrodes 42 or electrical connection pads 44 along a longitudinal length of the circuit trace 40. Where the circuit traces 40 are branched, the plural electrodes 42 may send and receive electrical signals from spatially separate regions of body tissue in which the framework support member 32 is implanted. In this case, the plural signals may be identical signals or may be multiplexed electrical signals.

The integrated circuit medical device of the present invention integrally and substantially monolithically combines a framework support member 32 with an integral and monolithic sensor member at the electrodes 42 or electrical connector pads 44. Microelectronic components may be coupled to the sensor member or may be formed as an integrated circuit on the sensor member wherein the sensor member is the substrate for the microelectronic components. The microelectronic component may be configured as an LC circuit, an amplifier, a transmitter, filter, tuner, power supply, an analog-digital converter, memory, computer, sensor or any such other microelectronic component as is capable of being formed integrally and substantially monolithically with the circuit traces 40 of the integrated circuit medical device 30. Such microelectronic components may be formed on the end pads 42 by vacuum deposition processes, 3D printing, photolithography or other such microelectronic processing techniques as are well known in the microelectronic processing field.

The framework support member 32 is preferably formed by vacuum depositing a device-forming material onto a substrate. The device-forming material is preferably an electrically conductive material suitable for transmitting electromagnetic signals into a body tissue and including a flexibility. Of course, because it is implantable, the medical device must also be biocompatible. According to one embodiment, a shape memory alloys or superelastic alloys metal, such as Nitinol, are well suited both as the device-forming material and the sensing device. Binary, ternary, quaternary or other metal alloys may be employed as the device-forming. Non-limiting examples include NiTi, NiTiCo, NiTiPt, NiTiPd, NiTiHf, NiTiZr, NiTiAu, NiTiCr, NiTiW, NiTiCoZr, or NiTiCuPd. Electrically conductive polymers are also contemplated within the scope of the invention as the material for the framework support member 32.

The framework support member 32 may be configured into a tubular shape, a planar shape or into complex geometric shapes conforming to the body region into which it is implanted. The framework support member 32 has a plurality of openings passing through a thickness of the framework support member 32 which are configured to geometrically deform to allow for multi-axial compliance and flexibility of the framework support member 32. The plurality of openings bound a plurality of structural members in the framework support member 32. A plurality of slots 58 is present in at least some of the structural members. The slots 58 define circuit traces 40 in the structural members between adjacent pairs of slots 58. A dielectric material 38 is filled into the slots 58 to electrically isolate the circuit traces 40 from the remainder of the structural member 34 in which the slot opening 58 is present. A coating of the dielectric material 38 covers the framework support member 32 and leaves exposed regions of circuit traces 40 for a passive or active sensor on one end of the circuit trace and for an electrical connection to the circuit traces 40 at an opposing end of the circuit traces 40.

The electrodes 42, or additional electrical connector pads 44, are electrically coupled to the electrical connector pads 44 via the circuit traces 40. Electrical leads or a plurality of electrical conduits (not shown) are coupled to the electrical connector pads 44 to conduct electrical energy through the circuit traces 40 to the electrodes 42 or additional electrical connector pads 44. In this manner, the electrodes 42 or additional electrical connection pads 44 may be electrically coupled to the soft or hard tissue adjacent the integrate circuit medical device.

In another embodiment to further facilitate electrically coupling the electrodes 42 to the adjacent tissue, the electrodes may have raised surface topographical features, such as tissue contacting or tissue penetrating projections, such as, for example, micro-needles, that engage the tissue allowing for better electrical contact between the electrodes and the tissue.

Figure 3A:
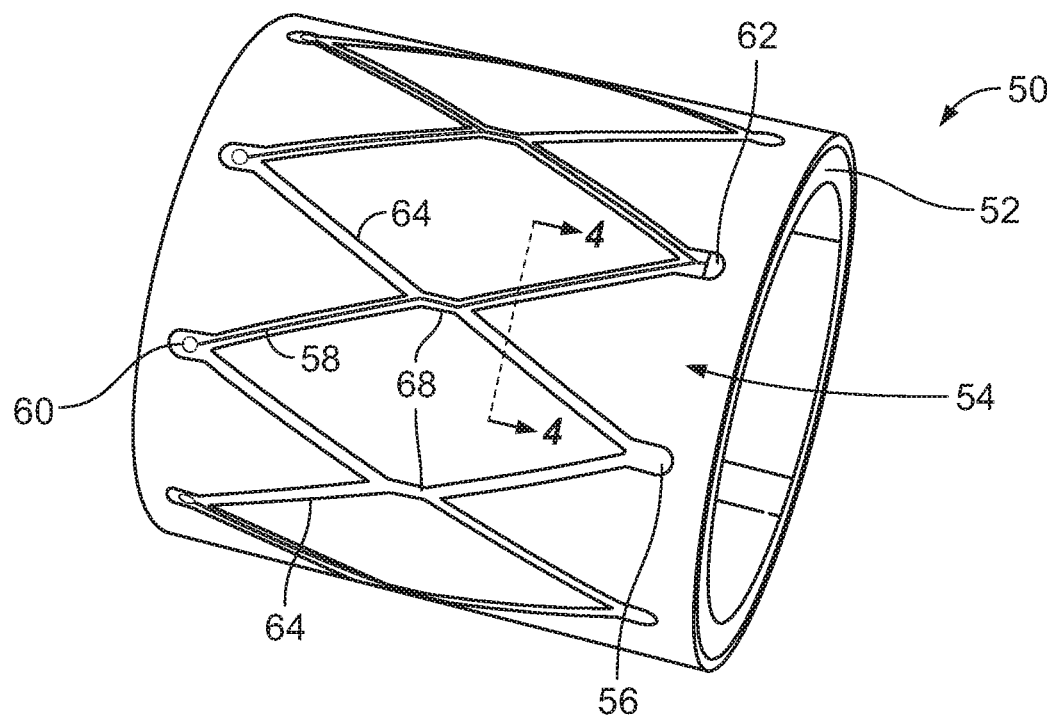
FIG. 3A-3B are perspective views of a patterned film deposited onto a substrate in accordance with methods of the present invention.

FIGS. 3A-9A and FIGS. 3B-9B sequentially illustrate the process stages of making the integrated circuit medical device 100 according to the method 10 of the present invention. FIGS. 3A and 4A depict the device 50 at process step 14*a* wherein the device forming material 54 is deposited onto substrate 52 and patterned to form the pattern of the integrated circuit medical device 30 with the framework support member 56, the structural members 64, the slots 58, the end pads 60 and the connection pads 62 being formed in the device forming material 54 on the substrate 52.

Figure 5A:
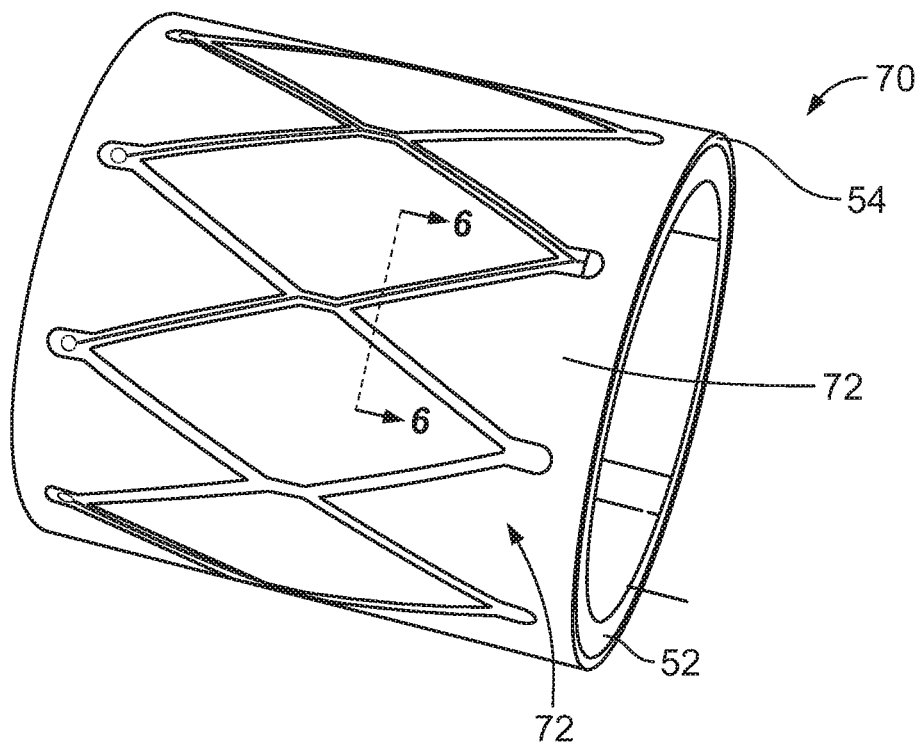
FIGS. 5A-5B are perspective views of a dielectric coating over the patterned film on the substrate in accordance with the methods of the present invention.
Figure 6A:
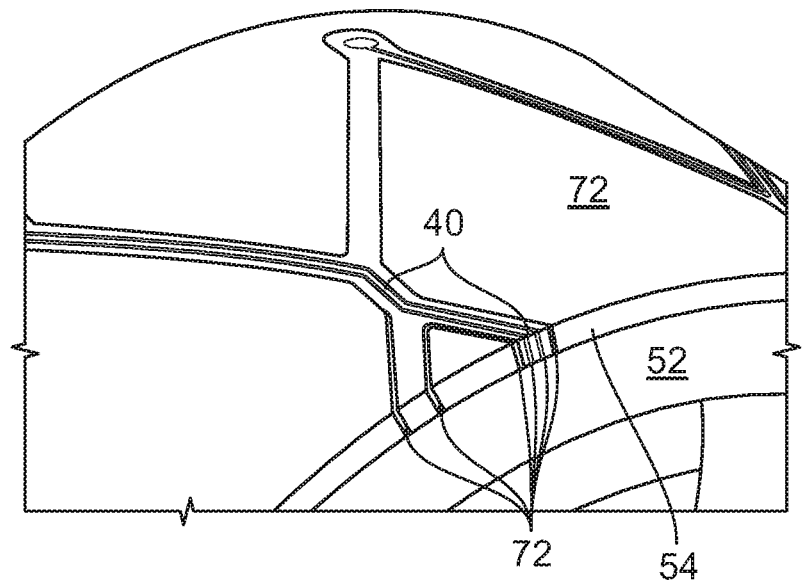
FIGS. 6A-6B are cross sectional views taken along line 6-6 of FIGS. 5A-5B.

FIGS. 5A and 6A depict the device 70 at process step 16, where the dielectric material coating 72 is formed over the entire outer surface of the device forming material 54 while it is still on the substrate 52. The dielectric material coating 72 fills the slots 58 in the device forming material 54.

Figure 7A:
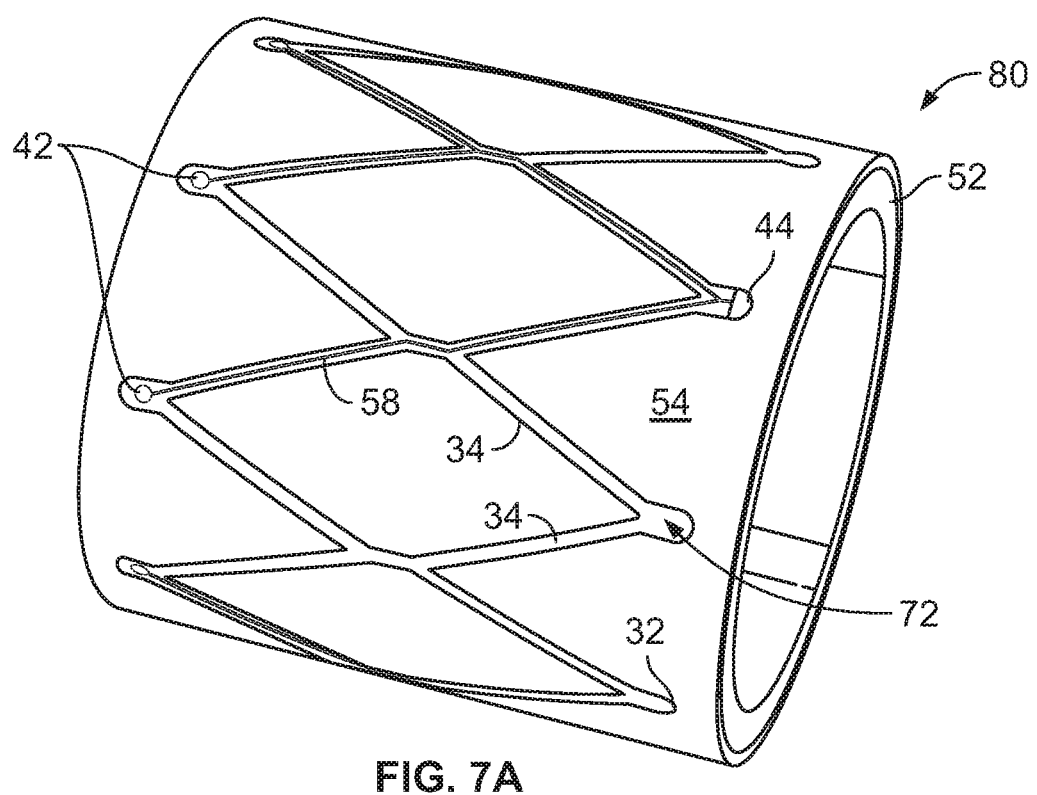
FIGS. 7A-7B are perspective views of the dielectric coating on the patterned portions of the deposited film on the substrate in accordance with the method of the present invention.

FIG. 7A depicts the device 80 at process step 18, where the dielectric material coating 72 is selectively removed from the device forming film 54 while it is still on the substrate 52, while leaving the dielectric material coating 72 on the framework support member 32, the structural members 34, the circuit traces 40 and filling the slots 58. The dielectric material coating 72 is also removed from the end pads 42 and connection pads 44.

Figure 8A:
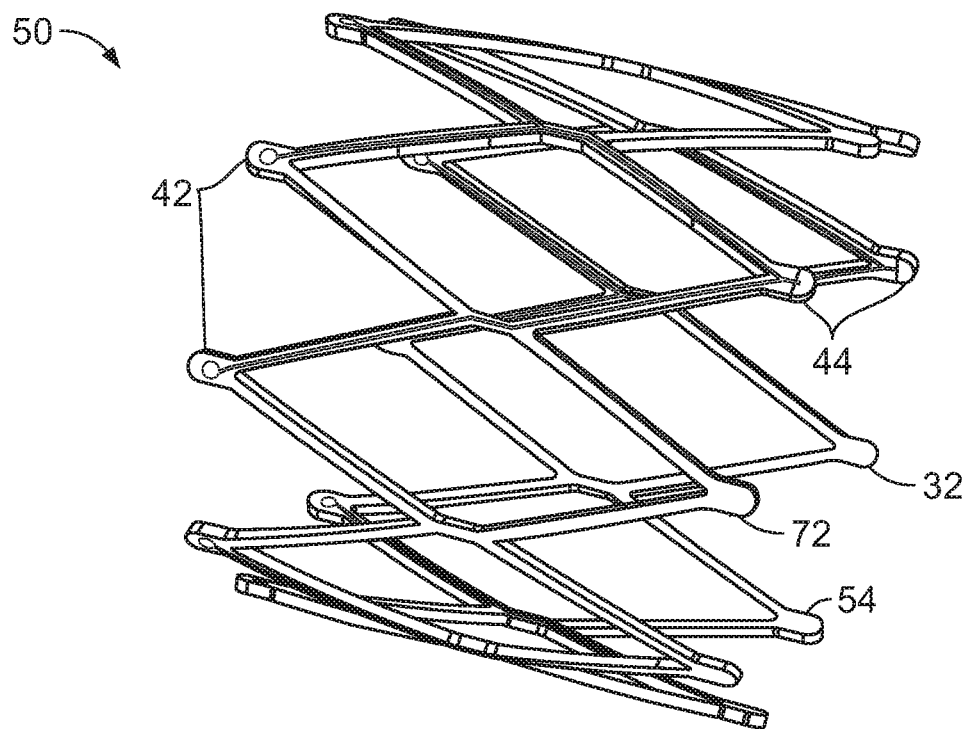
FIGS. 8A-8B are perspective views of the integrated circuit medical device framework platform released from the patterned film and substrate in accordance with the method of the present invention.

FIG. 8A depicts the device 90 at process step 20, where the substrate 52 has been removed from the framework support member 32 leaving the framework support member 32 with the dielectric material coating 72 only on lateral surfaces and one outer surface of the framework support member 32. A second outer surface of the framework support member 32, which was in intimate contact with the substrate 52, now removed, has exposed device forming material 54 as it was not exposed when the dielectric material coating 72 was applied.

Figure 9A:
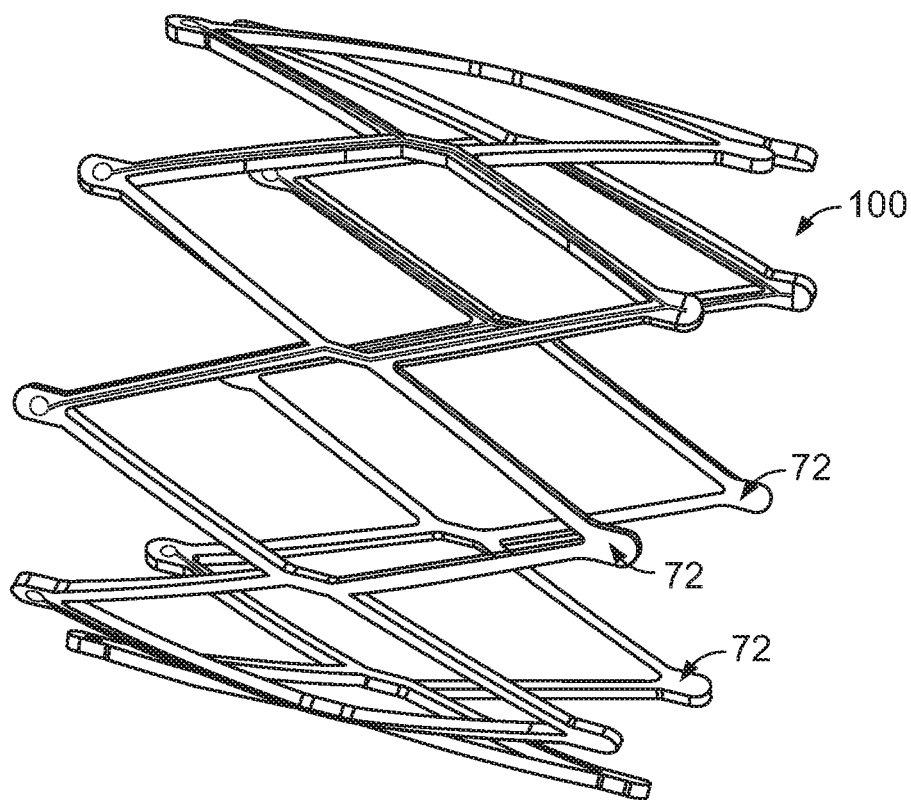
FIGS. 9A-9B are perspective views of the integrated circuit medical device framework platform with a complete dielectric coating on all surfaces thereof.

FIG. 9A depicts the device 100 at process step 22, where a second coating of dielectric material 72 is applied to all surfaces of the framework support member 32, including both outer surfaces and all lateral surfaces, including the end pads 42 and connection pads 44. Selective removal of the dielectric material coating 72 on the end pads 42 and connection pads 44 from process step 24 yields the integrated circuit medical device 30 as depicted in FIG. 2.

Figure 3B:
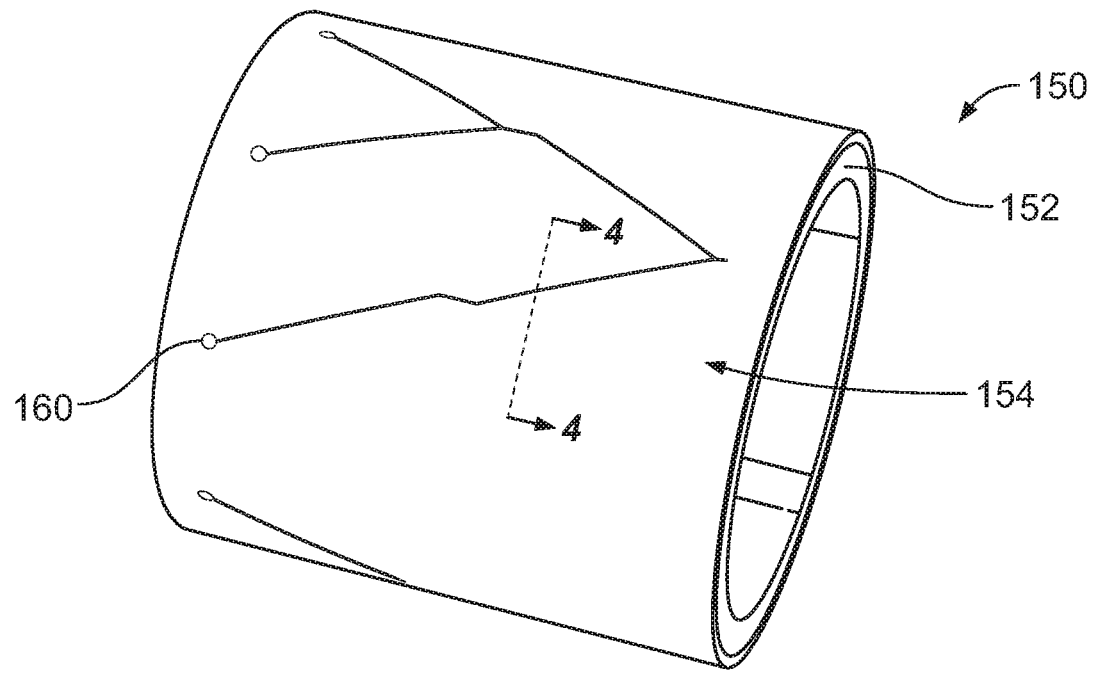
Figure 4A:
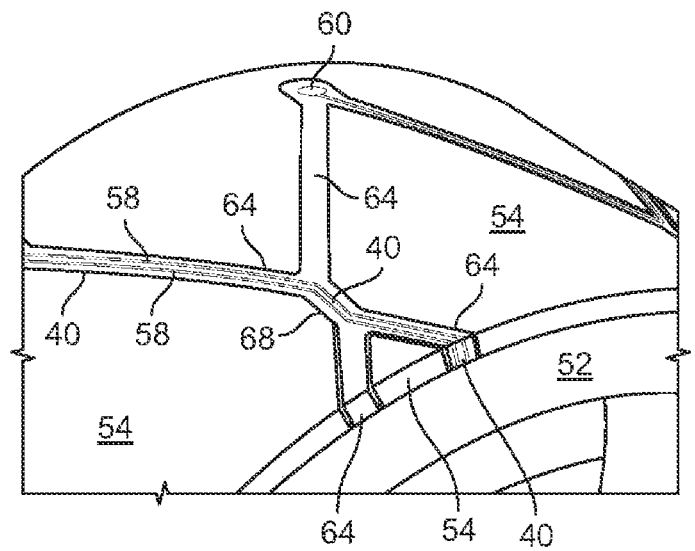
FIGS. 4A-4B are cross-sectional views taken along line 4-4 of FIGS. 3A-3B.
Figure 4B:
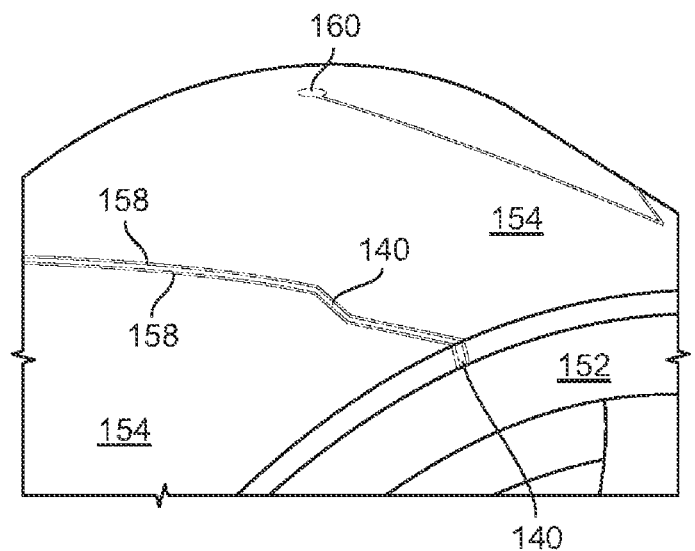

Alternatively, FIGS. 3B and 4B depict the device 150 at process step 14*b* wherein the device forming material 154 is deposited onto substrate 52 and patterned to form the pattern of the circuit traces 140 integrated circuit medical device 200.

Figure 5B:
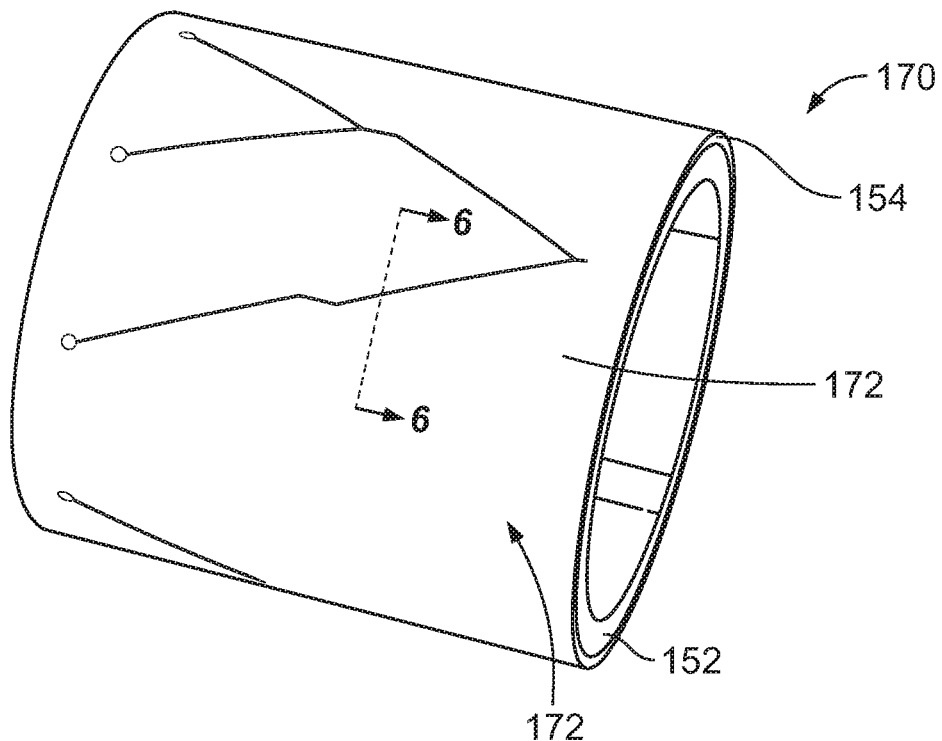
Figure 6B:
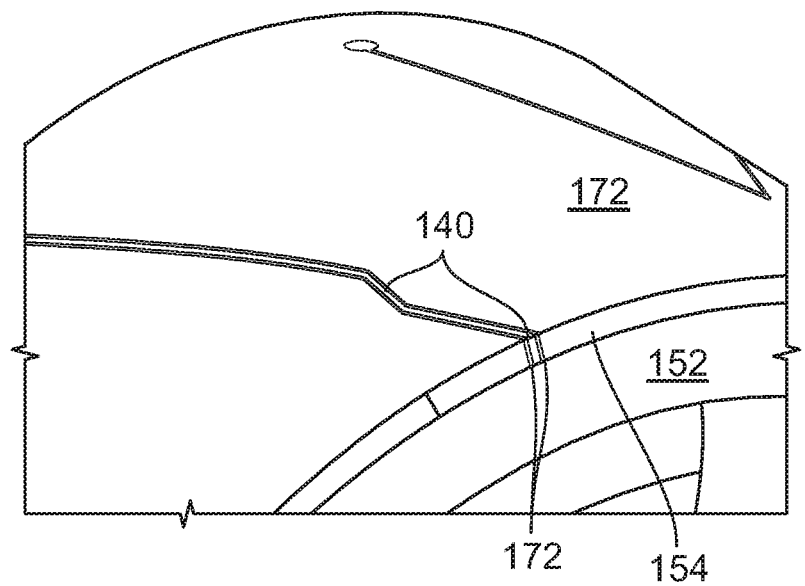

FIGS. 5B and 6B depict the device 170 at process step 16, where the dielectric material coating 172 is formed over the entire outer surface of the device forming material 54 while it is still on the substrate 152. The dielectric material coating 72 fills the slots 158 in the device forming material 54.

Figure 7B:
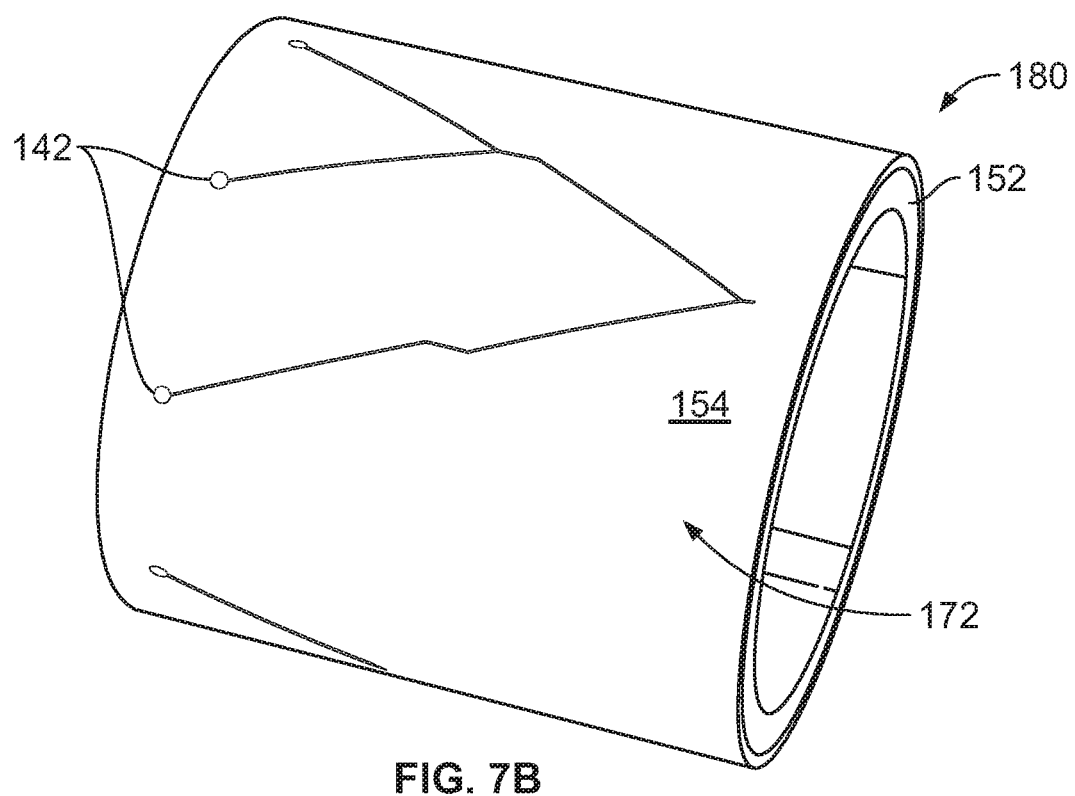

FIG. 7B depicts the device 80 at process step 18, the framework support member 156, the structural members 164, are being patterned in the device forming material 154 on the substrate 152 and where the dielectric material coating 172 is selectively removed from the device forming film 154 while it is still on the substrate 152, while leaving the dielectric material coating 172 on the framework support member 132, the structural members 134, the circuit traces 40 and filling the slots 58. The dielectric material coating 172 is also removed from the end pads 42 and connection pads 44.

Figure 8B:
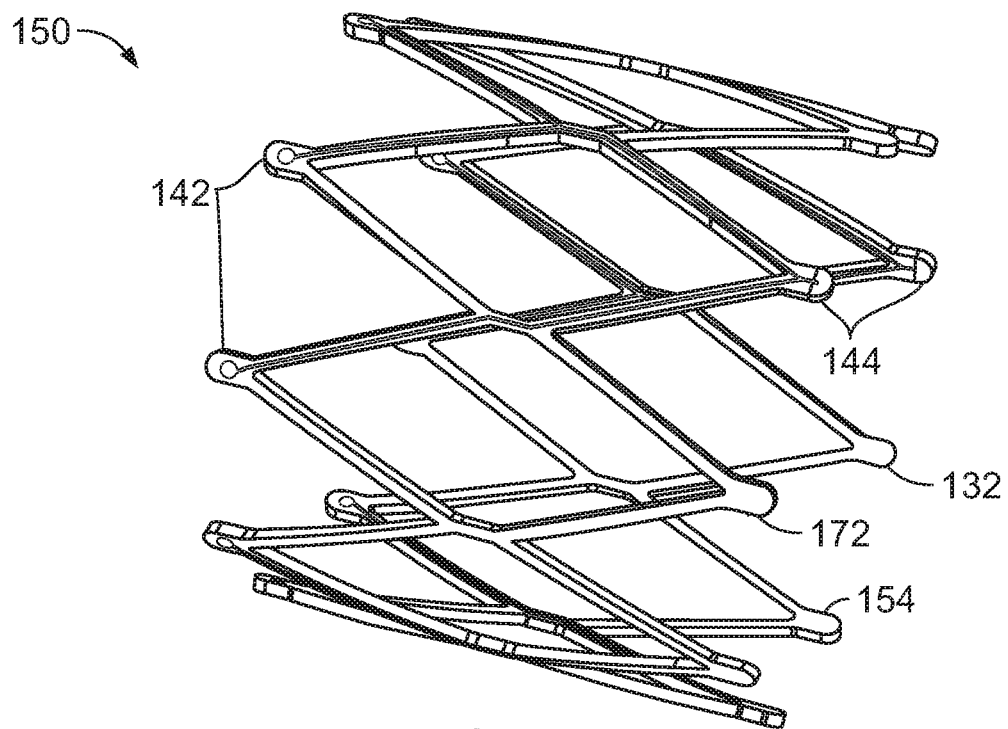

FIG. 8B depicts the device 190 at process step 20b, where the substrate 152 has been removed from the framework support member 132 leaving the framework support member 132 with the dielectric material coating 172 only on lateral surfaces and one outer surface of the framework support member 132. A second outer surface of the framework support member 132, which was in intimate contact with the substrate 152, now removed, has exposed device forming material 154 as it was not exposed when the dielectric material coating 172 was applied.

Figure 9B:
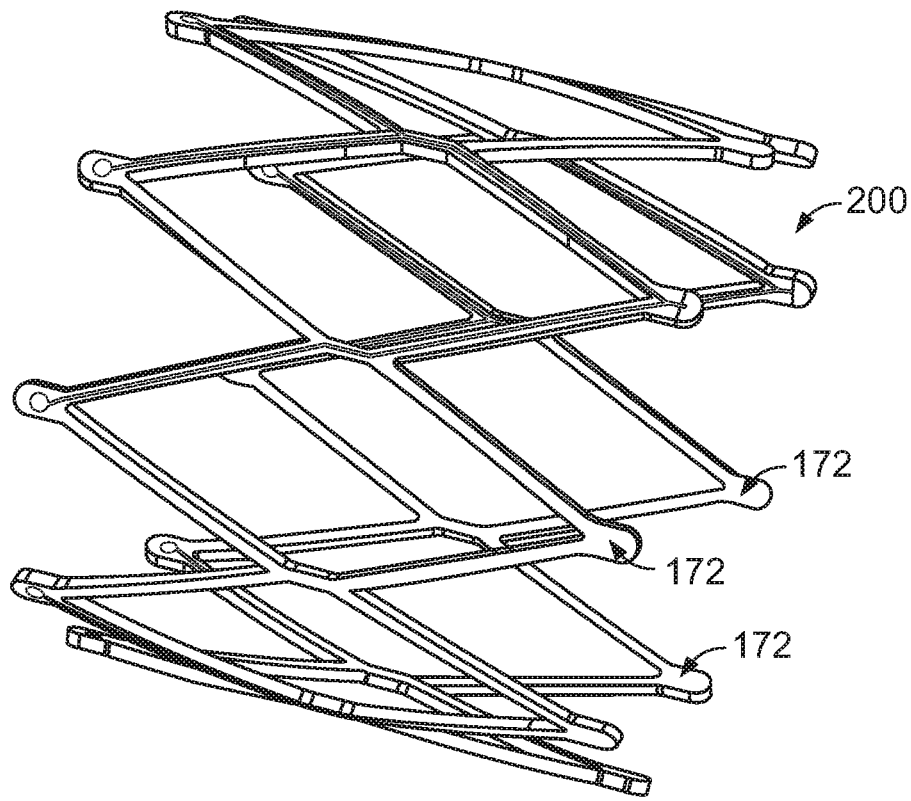
Figure 10A:
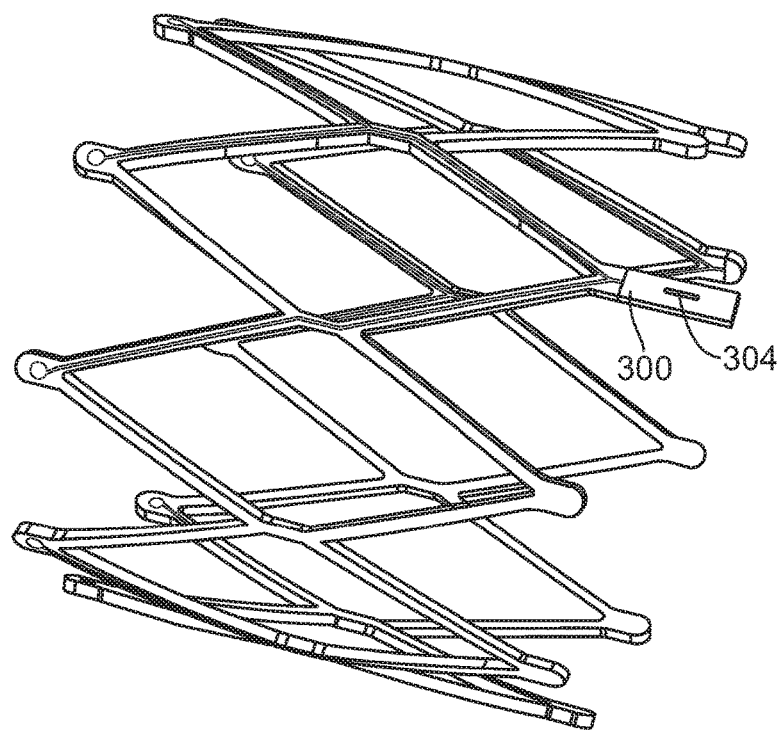
FIGS. 10A-10C are perspective views of the extension member and connections thereto in accordance with an embodiment of the present invention.
Figure 10B:
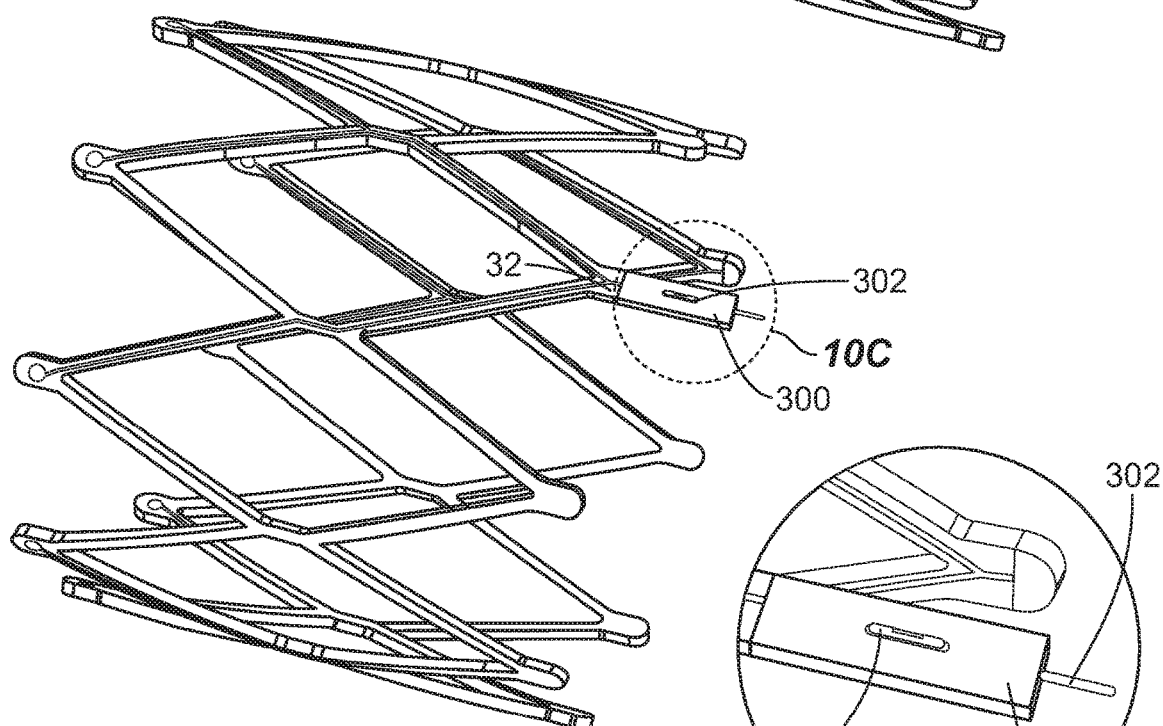
Figure 10C:
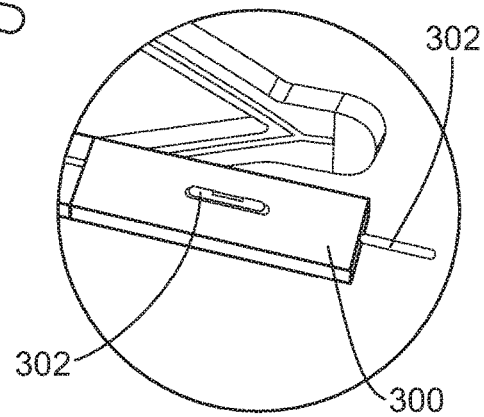
Figure 11A:
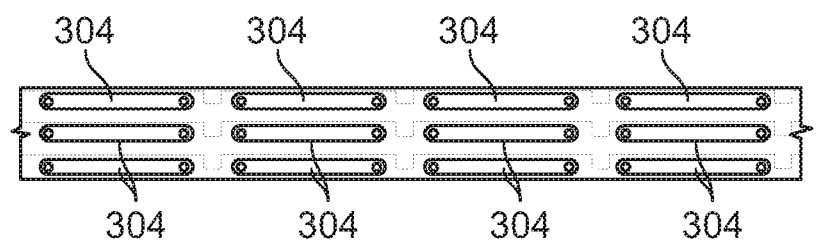
FIGS. 11A-11B are perspective and flat views of additional embodiments of the extension member and connections thereto in accordance with an embodiment of the present invention.
Figure 11B:
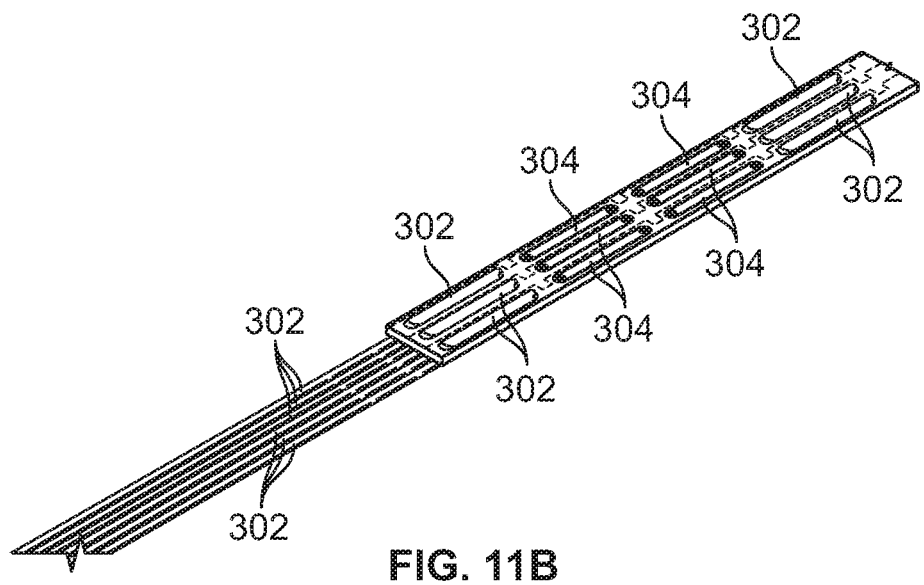

FIG. 9B depicts the device 200 at process step 22b, where a second coating of dielectric material 172 is applied to all surfaces of the framework support member 132, including both outer surfaces and all lateral surfaces, including the electrodes 42 and electrical connection pads 44. Selective removal of the dielectric material coating 72 on the end pads 42 and connection pads 44 from process step 24 yields the integrated circuit medical device 30 as depicted in FIG. 2.

In some embodiments as shown in FIGS. 10A-10C and 11A-B the structural frame member 30 may comprise an extension member 300 or a plurality of extension members 300 projecting from the structural frame member 32. The extension members may further comprise a plurality of electrical connector pads 44 terminating or beginning new circuit traces 40. Each electrical connector pad 44 electrically coupled through an electrical lead 302 or electrical conduit 302 to an external data acquisition device, power supply, or ground as described above. The electrical leads or electrical conduits 302 may be coated with a dielectric coating 38. In some embodiments, the extension members 300 may further comprise plural electrical lead or electrical conduit openings within depressions, recesses or grooves 304 configured as electrical connector pads allowing the electrical lead or electrical conduit 302 to be coupled to the respective electrical trace 40 mid-plane the extension member 300 and filled with a conductive solder or weld to reduce the thickness profile of the extension member 300.

Vacuum deposition onto both cylindrical and planar substrates is known in the art, as exemplified by U.S. Pat. Nos. 6,379,383 and 6,357,310, which are hereby incorporated by reference. Similarly, 3D printing onto cylindrical surfaces is also known in the art, as exemplified by WO 2011/011818, also incorporated by reference. 3D printing onto planar substrates is also well known and may be employed as well as an alternative to forming the physiological sensor device and/or the microelectronic components on the physiological sensor device.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

The invention claimed is:

1. A method of making an integrated circuit medical device, comprising the steps of:
   a. depositing a layer of an electrically conductive material onto a substrate forming a framework support member;
   b. forming a plurality of slots passing through the framework support member and to the substrate thereby defining a plurality of circuit traces bounded by the plurality of slots; and
   c. coating a dielectric layer onto the framework support member and plurality of traces thereby filling the plurality of slots and binding the plurality of circuit traces to the framework support member wherein the plurality of circuit traces are electrically isolated from the framework support member.

2. The method of claim 1, wherein the step of depositing a layer of an electrically conductive material comprises the step of depositing at least one of a plastically deformable, shape memory or superelastic material.

3. The method of claim 2, wherein the step of depositing a layer further comprises the step of sputter depositing.

4. The method of claim 1, further comprising the step of patterning the framework support member through the dielectric layer and the layer of electrically conductive material after the step of coating a dielectric layer.

5. The method of claim 4 wherein the step of patterning the framework support member further comprises defining a plurality structural members bounding the plurality of electrical traces and a plurality interstitial openings between structural members.

6. The method of claim 1, wherein the step of forming a plurality of slots further includes the step of retaining the framework support member and plurality of circuit traces on the substrate.

7. The method of claim 6, after step of patterning the framework, further comprising the step of releasing the substrate.

8. The method of claim 7, after the step of releasing the substrate, further comprising the step of coating a second dielectric layer over the entire medical device while masking the exposed at least one section of the at least one trace of the plurality of circuit traces.

9. The method of claim 8, after the step of coating a second dielectric layer, selectively removing regions of the dielectric layer or second dielectric layer to expose at least one section of at least one trace of the plurality of circuit traces.

10. The method of claim 8, further comprising the step of polishing a surface of the framework support member after releasing the substrate prior to the step of coating a second dielectric layer.

11. The method of claim 1 wherein the step of forming a plurality of slots further comprises the step of defining and bounding at least one connector pad of at least one circuit trace of the plurality of circuit traces.

12. The method of claim 11, wherein the step of defining and bounding at least one connector pad further comprises the step of defining at least one of an electrode and an electrical connector pad.

13. The method of claim 12, wherein the electrode is configured to interface with the body.

14. The method of claim 12, wherein the connector pad is electrically isolated from the body.

15. The method of claim 1 wherein the step of coating a dielectric layer comprises the step of coating a polyimide layer.

16. The method of claim 1, further comprising the step of electrically coupling the plurality of circuit traces to a plurality of electrical conduits or electrical leads.

17. The method of claim 1, further comprising the step of depositing a second layer of electrically conductive material onto the dielectric layer defining at least a second electrical trace layer.

18. The method of claim 17, further comprising the step of depositing a second dielectric coating layer onto the second layer of electrically conductive material.

19. The method of claim 18, further comprising the step of sequentially depositing electrically conductive material layers and dielectric coating layers.

20. The method of claim 1, after the step deposing a layer of electrically conductive material, forming an alignment marker and registering the alignment marker to maintain a consistent patterning position used in the step of forming a plurality of slots.

* * * * *